US009616169B2

(12) United States Patent
Lafferty et al.

(10) Patent No.: US 9,616,169 B2
(45) Date of Patent: Apr. 11, 2017

(54) POWER INJECTOR WITH STATUS MESSAGING

(75) Inventors: Sean B. Lafferty, Taylor Mill, KY (US); David P. Humeniuk, Cincinnati, OH (US)

(73) Assignee: Liebel-Flarsheim Company LLC, Cincinnati, OH (US)

( * ) Notice: Subject to any disclaimer, the term of this patent is extended or adjusted under 35 U.S.C. 154(b) by 520 days.

(21) Appl. No.: 12/742,930

(22) PCT Filed: Nov. 19, 2008

(86) PCT No.: PCT/US2008/012908
§ 371 (c)(1),
(2), (4) Date: May 14, 2010

(87) PCT Pub. No.: WO2009/067206
PCT Pub. Date: May 28, 2009

(65) Prior Publication Data
US 2010/0293496 A1    Nov. 18, 2010

Related U.S. Application Data

(60) Provisional application No. 60/988,834, filed on Nov. 19, 2007.

(51) Int. Cl.
*G06F 19/00*    (2011.01)
*A61M 5/145*    (2006.01)

(52) U.S. Cl.
CPC ..... *A61M 5/14546* (2013.01); *G06F 19/3406* (2013.01); *G06F 19/3468* (2013.01); *A61M 2005/14553* (2013.01); *A61M 2205/502* (2013.01); *G06F 19/321* (2013.01)

(58) Field of Classification Search
CPC ............ A61M 5/14546; G06F 19/3468; G06F 19/3406; G06F 19/3481
USPC .................................................... 715/772
See application file for complete search history.

(56) References Cited

U.S. PATENT DOCUMENTS

| 4,854,324 | A | * | 8/1989 | Hirschman et al. | .......... 600/432 |
| 4,908,603 | A | * | 3/1990 | Yamaue et al. | ............... 340/525 |
| 5,276,796 | A | * | 1/1994 | Yamada et al. | ............... 715/803 |
| 5,573,515 | A | * | 11/1996 | Wilson et al. | ................ 604/236 |
| 5,782,805 | A | * | 7/1998 | Meinzer | ................ A61M 5/172 604/131 |
| 5,795,317 | A | * | 8/1998 | Brierton | .............. A61M 1/3624 494/35 |

(Continued)

FOREIGN PATENT DOCUMENTS

CN    101039711    9/2007
EP    0319272 A2    6/1989
(Continued)

*Primary Examiner* — Steven Sax
*Assistant Examiner* — Conrad Pack
(74) *Attorney, Agent, or Firm* — Marsh Fischmann & Breyfogle LLP

(57) ABSTRACT

A status messaging protocol (140) for a power injector (10) is disclosed. A setup screen (230) may be displayed on a graphical user interface (11) associated with the power injector (10). A status message (268) is displayed in a status message zone (266) on the setup screen (230). As the status of the power injector (10) changes, the status message (268) in the status message zone (266) on the setup screen (230) is updated.

9 Claims, 12 Drawing Sheets

(56) References Cited

U.S. PATENT DOCUMENTS

| | | | |
|---|---|---|---|
| 5,814,015 A * | 9/1998 | Gargano et al. | 604/67 |
| 6,055,985 A * | 5/2000 | Bae | A61M 5/14546 600/431 |
| 6,137,470 A * | 10/2000 | Sundstrom et al. | 715/786 |
| 6,173,316 B1 * | 1/2001 | De Boor et al. | 709/218 |
| 6,525,721 B1 * | 2/2003 | Thomas et al. | 345/600 |
| 6,643,537 B1 * | 11/2003 | Zatezalo | A61M 5/1452 600/431 |
| 2001/0025189 A1 | 9/2001 | Haueter et al. | |
| 2001/0044738 A1 * | 11/2001 | Elkin et al. | 705/8 |
| 2002/0007116 A1 | 1/2002 | Zatezalo et al. | |
| 2002/0055997 A1 * | 5/2002 | Pinnell | 709/224 |
| 2002/0097194 A1 * | 7/2002 | Uchida et al. | 345/3.1 |
| 2002/0151804 A1 | 10/2002 | O'Mahony et al. | |
| 2002/0198496 A1 | 12/2002 | Duchon et al. | |
| 2003/0018252 A1 * | 1/2003 | Duchon | A61B 6/481 600/432 |
| 2004/0024361 A1 * | 2/2004 | Fago et al. | 604/152 |
| 2004/0172588 A1 * | 9/2004 | Mattaway | 715/500.1 |
| 2004/0225255 A1 * | 11/2004 | Ono | 604/65 |
| 2005/0017582 A1 * | 1/2005 | Young | 307/64 |
| 2005/0113754 A1 | 5/2005 | Cowan | |
| 2005/0182323 A1 | 8/2005 | Grispo et al. | |
| 2005/0182371 A1 * | 8/2005 | Wagner et al. | 604/218 |
| 2006/0079768 A1 | 4/2006 | Small et al. | |
| 2006/0079842 A1 * | 4/2006 | Small et al. | 604/151 |
| 2006/0079843 A1 * | 4/2006 | Brooks et al. | 604/151 |
| 2006/0178616 A1 * | 8/2006 | Hartman et al. | 604/65 |
| 2006/0184008 A1 * | 8/2006 | Zatezalo et al. | 600/420 |
| 2006/0236269 A1 * | 10/2006 | Borna | 715/963 |
| 2006/0265626 A1 * | 11/2006 | Thorisson et al. | 714/12 |
| 2007/0083152 A1 * | 4/2007 | Williams et al. | 604/65 |
| 2007/0097137 A1 * | 5/2007 | Walton et al. | 345/581 |
| 2007/0124351 A1 * | 5/2007 | Nakazawa | 708/130 |
| 2007/0213662 A1 * | 9/2007 | Kalafut | A61M 5/14546 604/96.01 |
| 2007/0268280 A1 * | 11/2007 | Fujita et al. | 345/204 |
| 2007/0282263 A1 * | 12/2007 | Kalafut | A61M 5/14546 604/131 |
| 2008/0177126 A1 * | 7/2008 | Tate | A61M 5/172 600/5 |
| 2008/0188841 A1 * | 8/2008 | Tomasello et al. | 606/11 |
| 2009/0038847 A1 * | 2/2009 | Muona et al. | 175/26 |

FOREIGN PATENT DOCUMENTS

| | | |
|---|---|---|
| EP | 1681069 A1 | 7/2006 |
| EP | 1776975 A2 | 4/2007 |
| WO | 96/36389 A1 | 11/1996 |
| WO | 00/10628 A2 | 3/2000 |
| WO | 2006/110851 A2 | 10/2006 |
| WO | 2007/033010 A1 | 3/2007 |
| WO | 2007062315 A2 | 5/2007 |

* cited by examiner

POWER INJECTOR WITH STATUS MESSAGING

CROSS-REFERENCE TO RELATED APPLICATIONS

This patent application is a U.S. National Stage of PCT/US2008/012908, filed 19 Nov. 2008, which claims priority to and is a non-provisional application of U.S. Provisional Patent Application Serial No. 60/988,834, that is entitled "POWER INJECTOR WITH STATUS MESSAGING," and that was filed on Nov. 19, 2007. Priority is claimed to each patent application set forth in this Cross-Reference to Related Applications section.

FIELD OF THE INVENTION

The present invention generally relates to the field of delivering fluid and, more particularly, to providing status information in relation to this fluid delivery.

BACKGROUND

Various medical procedures require that one or more fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is appropriately interconnected with an appropriate syringe plunger driver that is incorporated into the powerhead, such that operation of the syringe plunger driver axially advances the associated syringe plunger. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

A first aspect of the present invention is embodied by a method of operation for a medical fluid delivery system. A first screen is displayed on a graphical user interface of the medical fluid delivery system, and this first screen includes a status message region, segment, or zone. Fluid is discharged from the medical fluid delivery system (e.g., to a fluid target). A plurality of status messages is displayed in the status message zone on the first screen. Each of these status messages is displayed at a separate time and is reflective of a then current status of the medical fluid delivery system (e.g., of a power injector being used to discharge fluid).

A second aspect of the present invention is embodied by a method of operation for a medical fluid delivery system. A first screen is displayed on a graphical user interface of the medical fluid delivery system, and this first screen includes a status message region, segment, or zone. Fluid is discharged from the medical fluid delivery system (e.g., to a fluid target). At least one status message is displayed in the status message zone on the first screen, along with a next action due message.

A third aspect of the present invention is embodied by a method of operation for a medical fluid delivery system. A first screen is displayed on a graphical user interface of the medical fluid delivery system, and this first screen includes a status message region, segment, or zone. Fluid is discharged from the medical fluid delivery system (e.g., to a fluid target). At least one status message is displayed in the status message zone on the first screen. A listing of a plurality of status messages may be selectively displayed on the graphical user interface.

A fourth aspect of the present invention is embodied by a power injector that includes a powerhead, a syringe plunger driver, a graphical user interface, and control logic. The control logic is configured to generate a first screen on a graphical user interface, where this first screen includes a status message region, segment, or zone. The control logic is further configured to display a plurality of status messages in this same status message zone on the first screen. Each of these status messages is displayed at a separate time and is reflective of a then current status of the power injector.

A fifth aspect of the present invention is embodied by a power injector that includes a powerhead, a syringe plunger driver, a graphical user interface, and control logic. The control logic is configured to generate a first screen on a graphical user interface, where this first screen includes a status message region, segment, or zone. The control logic is further configured to simultaneously display at least one status message and a next action due message in this same status message zone on the first screen.

A sixth aspect of the present invention is embodied by a power injector that includes a powerhead, a syringe plunger driver, a graphical user interface, and control logic. The control logic is configured to generate a first screen on a graphical user interface, where this first screen includes a status message region, segment, or zone. The control logic is further configured to selectively display a listing of status messages that each has been previously displayed in a corresponding status message zone on the graphical user interface.

Various refinements exist of the features noted in relation to each of the above-noted first through the sixth aspects of the present invention. Further features may also be incorporated in each of the above-noted first through the sixth aspects of the present invention as well. These refinements and additional features may exist individually or in any combination in relation to each of the first through the sixth aspects. That is, each of the following features that will be discussed are not required to be used with any other feature or combination of features unless otherwise specified. By way of initial summary, each of the various aspects may be used together in any and all combinations.

At least one screen with a status message region, segment, or zone is presented on at least one graphical user interface. Any such screen with a status message zone may be displayed on a graphical user interface at a single location or at multiple locations. In one embodiment, at least one screen with a status message zone is displayed on a graphical user interface associated with a power injector (e.g., on a powerhead, on a remote console, or both).

Color may be used to provide information in relation to any status message that is being displayed in a corresponding status message zone on a graphical user interface. For instance, the color of the background in which a status message is displayed in a corresponding status message zone may be utilized to convey status information. In the case where multiple status messages are sequentially displayed on some basis (e.g., in response to a change in the status of a power injector) in a corresponding status message zone, different colors may be used in relation to at least some of these status messages (e.g., the background color may be changed). In one embodiment, displaying a first color in relation to any status message displayed in a corresponding status message zone may be indicative of a normal condition, displaying a second color in relation to any status message displayed in a corresponding status message zone may be indicative of a cautionary condition, and displaying a third color in relation to any status message displayed in a corresponding status message zone may be indicative of an error condition.

The first screen may be any appropriate screen for purposes of executing a medical fluid delivery procedure or protocol. In one embodiment, the first screen is in the form of a setup screen. Such a setup screen may be utilized to enter/edit one or more parameters that each contribute to the execution of a medical fluid delivery procedure or protocol. A status message zone may be included on one or more screens that may be presented on a graphical user interface for purposes of executing a medical fluid delivery operation or protocol. In one embodiment, the status message zone is displayed at the same location on each of a plurality of different screens (e.g., on both a setup screen and a progress screen).

At least one status message may be displayed at all times in a status message zone on the first screen, although the status message may be changed from time to time based upon a status change of a medical fluid delivery system (e.g., a change in status of a power injector being used to deliver fluid). Previous-in-time status messages, which were previously displayed in a corresponding status message zone on a graphical user interface, may be displayed on a graphical user interface in the form of a list and in any appropriate manner. Each status message that has been generated and displayed in relation to a medical fluid delivery procedure or protocol may be retrieved and displayed in any appropriate manner. In one embodiment, a drop-down menu button alongside the status message zone may be activated/selected in any appropriate manner to produce a listing of status messages (e.g., in reverse chronological order). In another embodiment, a status message history button or the like on a graphical user interface may be activated/selected in any appropriate manner to produce a listing of status messages (e.g., in reverse chronological order), and this status message history button may be at any appropriate location in relation to the status message zone (e.g., on a different part of the first screen compared to the status message zone).

Each status message that is displayed in a corresponding status message zone may be of any appropriate type or in any appropriate form. In one embodiment, the status message is in the form of a textual status message. In another embodiment, the status message is in the form of a graphical status message (e.g., an icon). Any number of status messages of any appropriate type may be simultaneously displayed in any given status message zone (e.g., a single textual status message, along with one or more graphical status messages or icons).

Each graphical status message that is presented in a corresponding status message zone may convey an association with one or more tasks in any appropriate manner (e.g., by the shape of an icon, by associating an abbreviation with the icon). Each graphical status message may convey status information by being presentable in a plurality of different states. A particular graphical status message may be presentable in at least two different states. A particular graphical status message may be presentable in at least three different states. A particular graphical status message may be presentable in four different states. Representative states for graphical status messages include without limitation an inactive state (e.g., the associated task(s) is not currently being executed), an active state (e.g., the associated task(s) is currently being executed), a completed state (e.g., the associated task(s) has been completed), and a terminated state (e.g., the associated task(s) was undertaken, but not completed, for instance due to the existence of an error condition).

Other information may be presented in a corresponding status message zone. In one embodiment, a next action due message is displayed along with a status message in a corresponding status message zone. This next action due message may convey to an operator the next task that will be undertaken by a medical fluid delivery system (e.g., a power injector), may convey the next action to be undertaken by an operator, or both. In one embodiment, the next action due message relates to the status message currently being displayed in the corresponding status message zone.

Fluid may be discharged from a medical fluid delivery system (e.g., a power injector) to a fluid target in any appropriate manner. In one embodiment, fluid is injected into a fluid target. Any such fluid target may be of any appropriate size, shape, configuration, and/or type. In one embodiment, the fluid target is a patient of any appropriate type (e.g., a human, an animal).

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Any such power injector may be used for any appropriate application where the delivery of one or more fluids is desired, including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate). Any appropriate number of syringes may be integrated with any such power injector in any appropriate manner (e.g., detachably; front-loaded; rear-loaded; side-loaded), any appropriate fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a patient).

DETAILED DESCRIPTION

Figure 1:
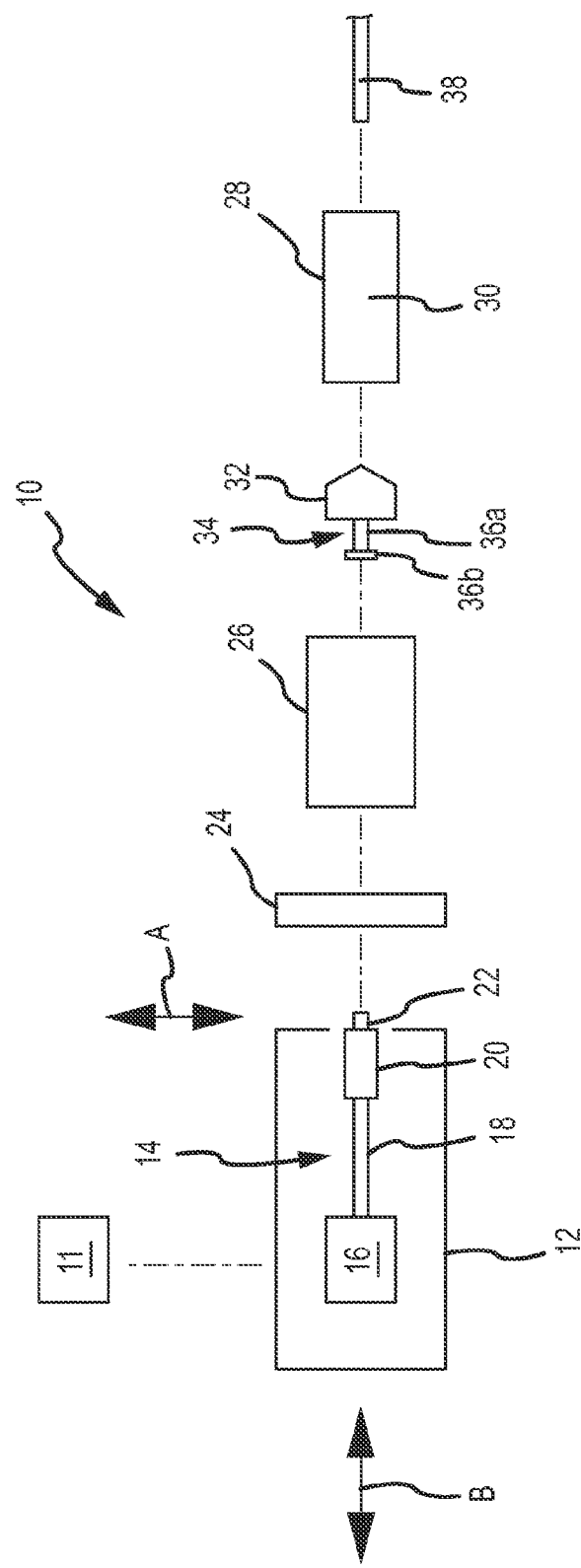
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically installed on the powerhead 12, followed by disposing the syringe 28 within the pressure jacket 26. The same pressure jacket 26 will typically remain installed on the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interfacing or interacting with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interface or interact with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 may interact with each syringe plunger 32 of the power injector 10 in any appropriate manner (e.g., by mechanical contact; by an appropriate coupling (mechanical or otherwise)) so as to be able to move or advance the syringe plunger 32 in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be required. In this case, the syringe plunger drive assembly 14 may be retracted for purposes of executing another fluid delivery operation (e.g., after another pre-filled syringe 28 is installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
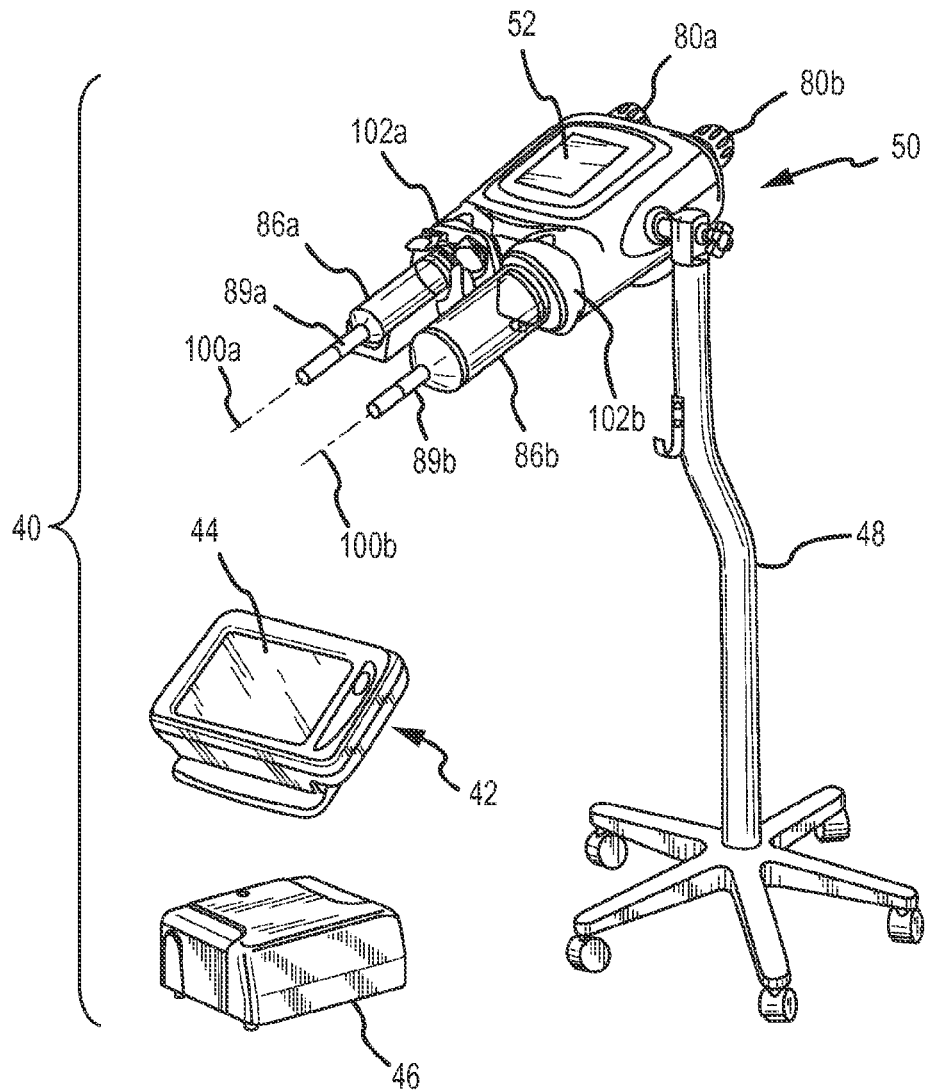
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 is mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
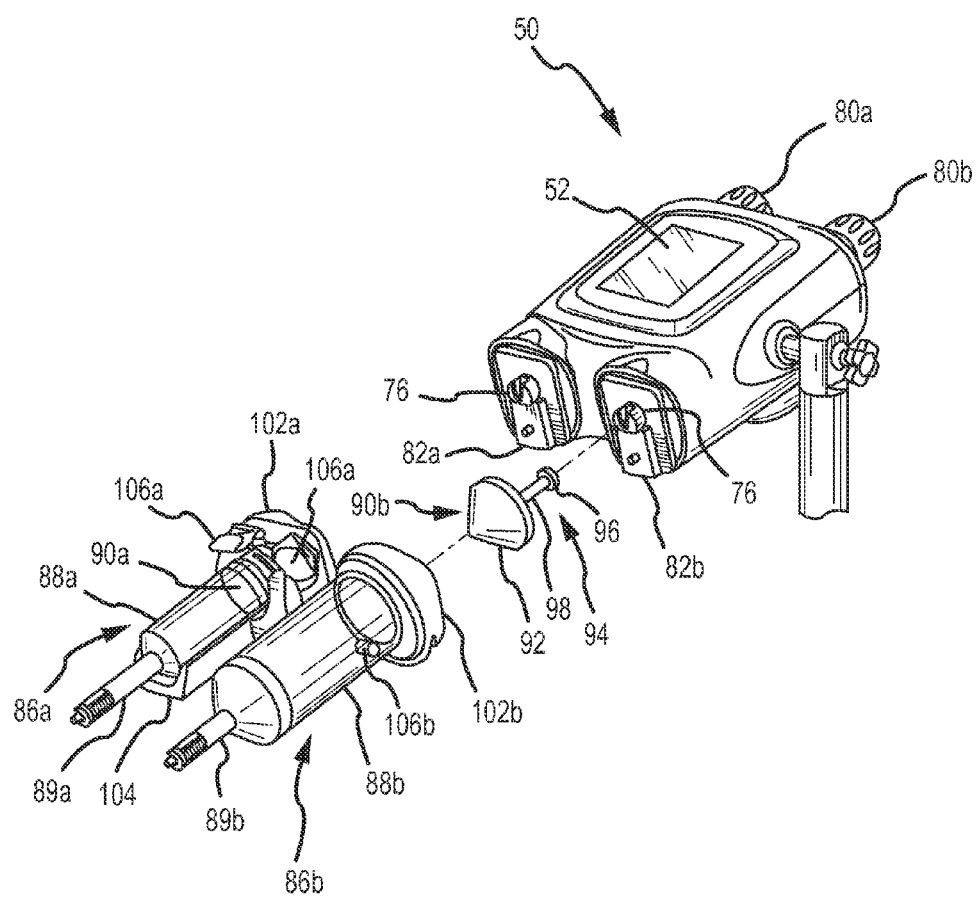
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within the syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74, which are each part of a syringe plunger drive assembly or syringe plunger driver 56 for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 86*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of handles 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74, which are each part of a syringe plunger drive assembly 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 may be moved relative to the powerhead 50 to move the syringe plunger 90*b* along the axis 100*b* (FIG. 2A). It may be such that the ram coupler 76 is engaged with, but not actually coupled to, the syringe plunger 90*b* when moving the syringe plunger 90*b* to discharge fluid through the nozzle 89*b* of the syringe 86*b*.

The faceplate 102*b* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*b* on and remove the faceplate 102*b* from its mounting 82*b* on the powerhead 50. The faceplate 102*b* also may be used to couple the syringe plunger 90*b* with its corresponding ram coupler 76 on the powerhead 50. In this regard, the faceplate 102*b* may include a handle 106*b*. Generally and with the syringe 86*b* being initially positioned within the faceplate 102*b*, the syringe 86*b* may be rotated along its long axis 100*b* (FIG. 2A) and relative to the faceplate 102*b*. This rotation may be realized by moving the handle 106*b*, by grasping and turning the syringe 86*b*, or both. In any case, this rotation moves/translates both the syringe 86*b* and the faceplate 102*b* at least generally within a plane that is orthogonal to the axes 100*a*, 100*b* (associated with movement of the syringe plungers 90*a*, 90*b*, respectively, and illustrated in FIG. 2A). Rotating the syringe 86*b* in one direction moves/translates the syringe 86*b* and faceplate 102*b* in an at least generally downward direction to couple the syringe plunger 90*b* with its corresponding ram coupler 76. Rotating the syringe 86*b* in the opposite direction moves/translates the syringe 86*b* and faceplate 102*b* in an at least generally upward direction to uncouple its syringe plunger 90*b* from its corresponding ram coupler 76.

As illustrated in FIG. 2B, the syringe plunger 90*b* includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90*b* and its corresponding ram coupler 76 are in a coupled state or condition. The syringe plunger 90*a* may include a similar syringe plunger coupler 94 for interfacing with its corresponding ram coupler 76.

Figure 2C:
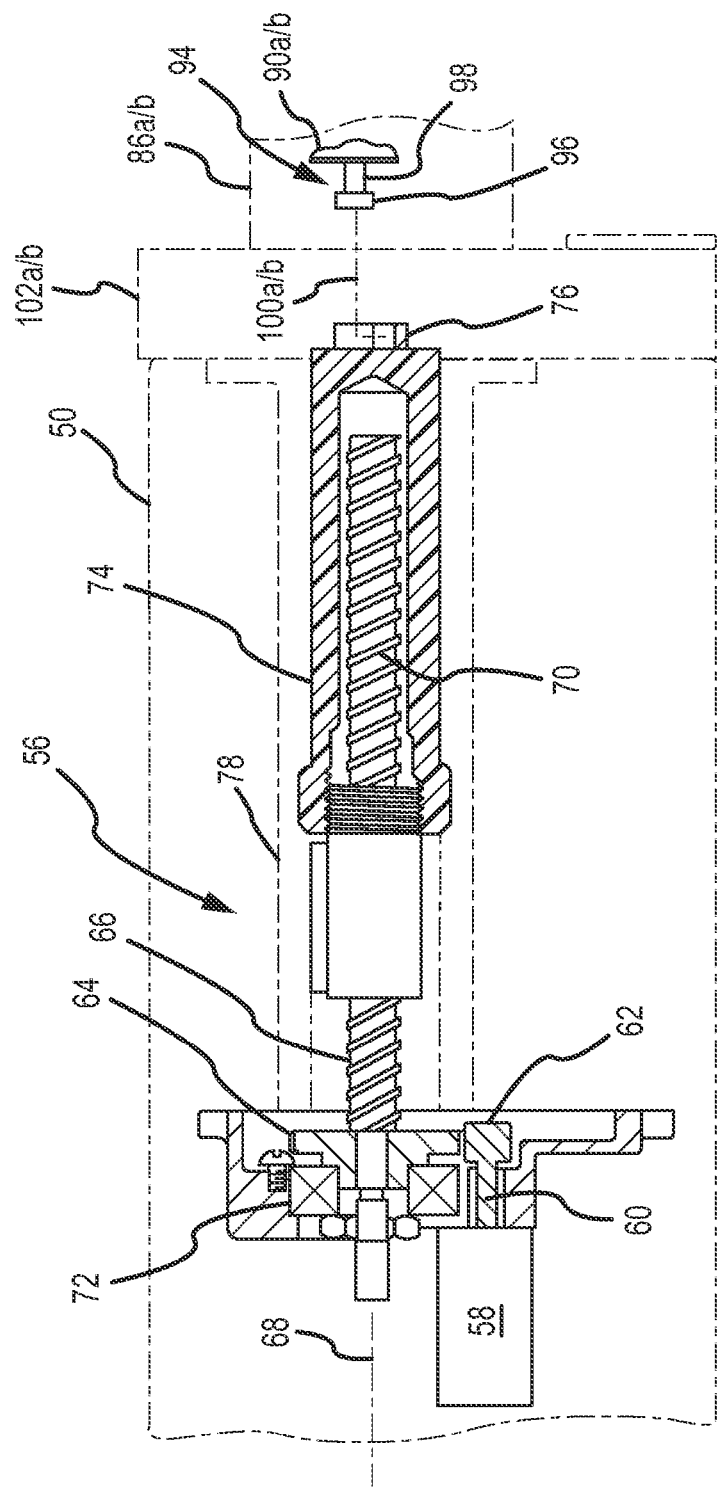
FIG. 2C is a schematic of one embodiment of a syringe plunger drive assembly used by the power injector of FIG. 2A.

The powerhead 50 is utilized to discharge fluid from the syringes 86*a*, 86*b* in the case of the power injector 40. That is, the powerhead 50 provides the motive force to discharge fluid from each of the syringes 86*a*, 86*b*. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86*a*, 86*b*. A separate syringe plunger drive assembly 56 may be incorporated into the powerhead 50 for each of the syringes 86*a*, 86*b*. In this regard and referring back to FIGS. 2A-B, the powerhead 50 may include hand-operated knobs 80*a* and 80*b* for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86*a/b*, while rotation of the drive screw 66 in the opposite direction axially advances the ram 74 along the drive screw 66 (and thereby along axis 68) away from the corresponding syringe 86*a/b*. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90*a/b* of the corresponding syringe 86*a/b*. When the ram coupler 76 and syringe plunger coupler 94 are appropriately coupled, the syringe plunger 90*a/b* moves along with ram 74. FIG. 2C illustrates a configuration where the syringe 86*a/b* may be moved along its corresponding axis 100*a/b* without being coupled to the ram 74. When the syringe 86*a/b* is moved along its corresponding axis 100*a/b* such that the head 96 of its syringe plunger 90*a/b* is aligned with the ram coupler 76, but with the axes 68 still in the offset configuration of FIG. 2C, the syringe 86*a/b* may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40 may include any appropriate fluid, for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
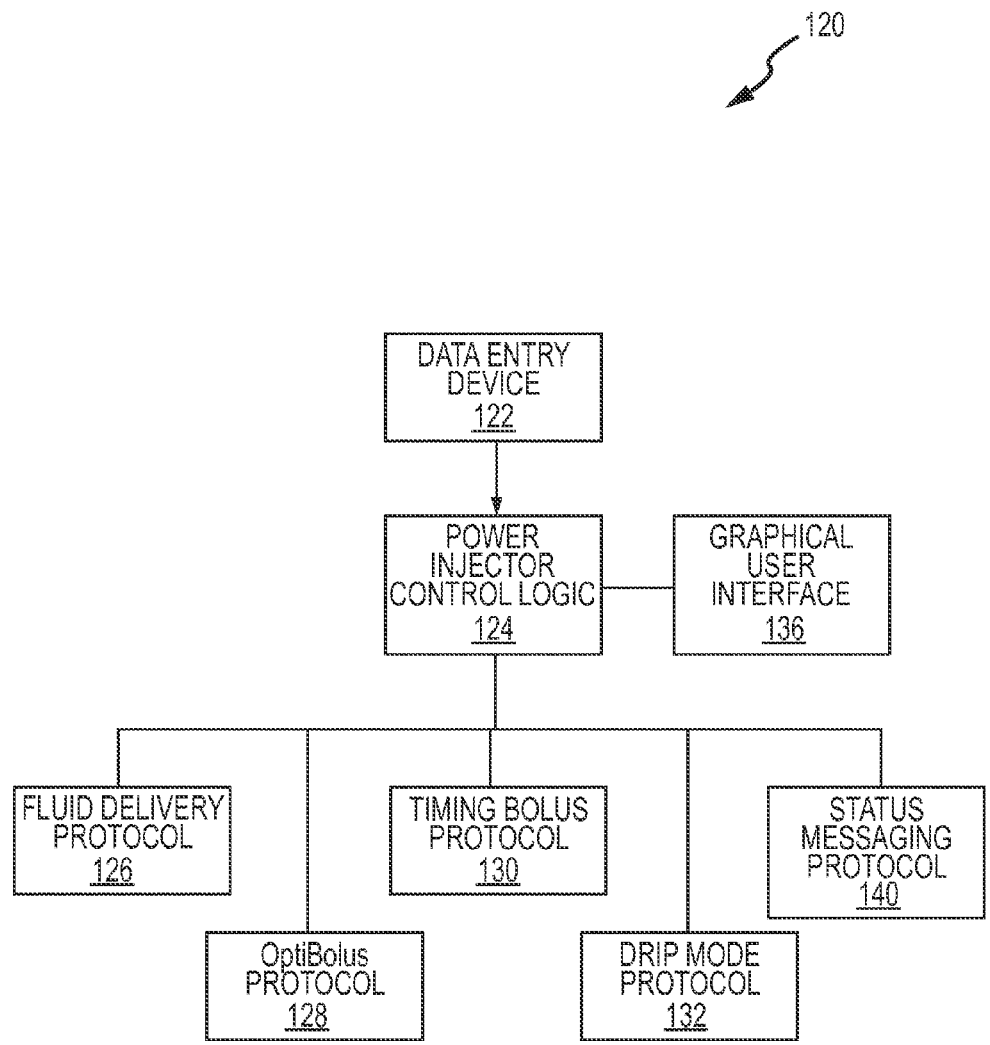
FIG. 3 is a schematic of one embodiment of control logic that may be used by the power injectors of FIGS. 1 and 2A-C.

FIG. 3 illustrates one embodiment of a power injector control system 120 that may be utilized by any appropriate power injector, including without limitation the power injector 10 of FIG. 1 and the power injector 40 of FIGS. 2A-C. The power injector control system 120 may include one or more data entry devices 122 of any appropriate configuration and/or type (e.g., a keyboard, a mouse, a touch screen display). One or more of these data entry devices 122 may be operatively interconnected with a power control injector module or power injector control logic 124. The power injector control logic 124 may be of any appropriate form and/or configuration, for instance software, hardware, firmware, and any combination thereof. At least one graphical user interface 136 (e.g., the graphical user interface 11 of the power injector 10) may be operatively interconnected with the power injector control logic 124 to present an appropriate output (e.g., to an operator of the corresponding power injector).

The power injector control logic 124 may be configured to include at least one fluid delivery or injection protocol 126 (e.g., for a medical application, and which may be referred to as a medical fluid delivery procedure or operation) and a status messaging protocol 140, and each of which may be in the form of a programmed sequence. For a medical fluid application, the protocol 126 thereby may be referred to as a medical fluid delivery protocol 126. Each fluid delivery protocol 126 may be configured to control the manner in which one or more fluids are being delivered to a fluid target, such as by being injected into a patient. A particular fluid delivery protocol 126 may be configured to deliver a programmed volume of a first fluid at a programmed flow rate, as well as a programmed volume of a second fluid at a programmed flow rate. Each delivery of each of the first and second fluids may be characterized as a phase. One or more phases may be utilized for each of the first and second fluids. In one embodiment, the first fluid is contrast media and the second fluid is saline. The status messaging protocol 140 will be discussed in more detail below, but generally is configured to provide status information (e.g., on the status of the power injector) in relation to the execution of a fluid delivery protocol 126.

The power injector control logic 124 of FIG. 3 may include one or more additional protocols as desired/required, and each of which may be in the form of a programmed sequence. Representative protocols that may be utilized by the power injector control logic 124 as desired/required, in addition to at least one fluid delivery protocol 126 and a status messaging protocol 140, include without limitation an OptiBolus® protocol 128, a Timing Bolus® protocol 130, and a drip mode protocol 132. Generally, the OptiBolus® protocol 128 may be configured to deliver an exponentially decaying flow rate injection that optimizes the contrast usage and provides an extended period of uniform enhancement of the area of interest. The Timing Bolus® injection protocol 130 may be configured to provide a timing bolus injection—a small volume of contrast media, followed by a small volume of saline—to a patient for purposes of determining the optimal scan delay needed to capture the contrast media in the area of interest. The drip mode protocol 132 may be configured to provide a drip injection—a low flow rate injection of a small volume of saline delivered to the patient to keep open the fluid pathway from the power injector to the patient.

Figure 4:
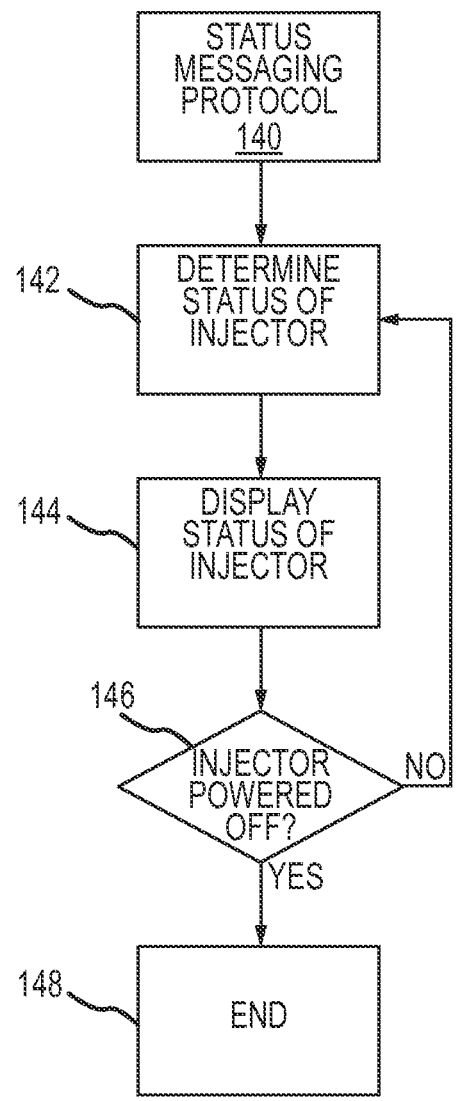
FIG. 4 is one embodiment of a status messaging protocol that may be used by the control logic of FIG. 3.

One embodiment of a status messaging protocol 140 is illustrated in FIG. 4, may be used by the control logic 124 of FIG. 3, and may be used by any appropriate power injector. The status messaging protocol 140 determines the status of the power injector (step 142). This status may be determined in any appropriate manner, for instance by various sensors, feedback loops, switches, or the like. The status of the power injector is displayed in accordance with step 144 (e.g., on one or more graphical user interfaces associated with a power injector). Injector status information may be conveyed in any appropriate manner and at any appropriate location or combination of locations. For instance, injector status information may be conveyed textually, graphically, or by a combination thereof. In one embodiment, injector status information is displayed on a graphical user interface that is associated with the power injector (e.g., on the powerhead; on a remote console).

The injector status may be updated on any appropriate basis in accordance with the status messaging protocol 140 of FIG. 4 (e.g., periodically). In the illustrated embodiment, the injector status is determined (142) and displayed (144) so long as the power injector is not in a "powered off" condition or state (step 146). That is, powering off the power injector may be used to terminate the status messaging protocol 140 (step 148).

The status messaging protocol 140 of FIG. 4 may be implemented in any appropriate manner. The injector status (step 142) may be continually displayed or displayed at all times (step 144) on at least one screen (e.g., a setup screen) that is presented on a graphical user interface associated with a power injector, including without limitation having the injector status (step 142) being continually displayed or displayed at all times (e.g., step 144) on each screen that is presented on a graphical user interface of a power injector in the execution of a fluid delivery protocol 126 (FIG. 3). Injector status information (step 142) may be displayed (step 144) at a common location on a plurality of screens that are each presented on a graphical user interface associated with a power injector, including without limitation where multiple, spaced-in-time injector status messages are displayed at the same location on a particular screen (e.g., on a setup screen) that is presented on a graphical user interface associated with a power injector.

The displaying of one or more status messages in accordance with step 144 of the status messaging protocol 140 of FIG. 4 may convey injector status information in one or more manners. For instance, color may be used in combination with a particular status message (e.g., textual; graphical; both textual and graphical) to convey injector status information. In one embodiment, one color (e.g., white or green) may be used in combination with at least one status message to indicate the existence of a normal condition, another color (e.g., yellow) may be used in combination with at least one status message to indicate the existence of a cautionary condition, while yet another color (e.g., red) may be used in combination with at least one status message to indicate the existence of an error condition. Although the color of the status message itself could be changed to provide color-based status information, in one embodiment it is the color of the background (in which the status message is presented) that is used to provide color-based status information.

Figure 5:
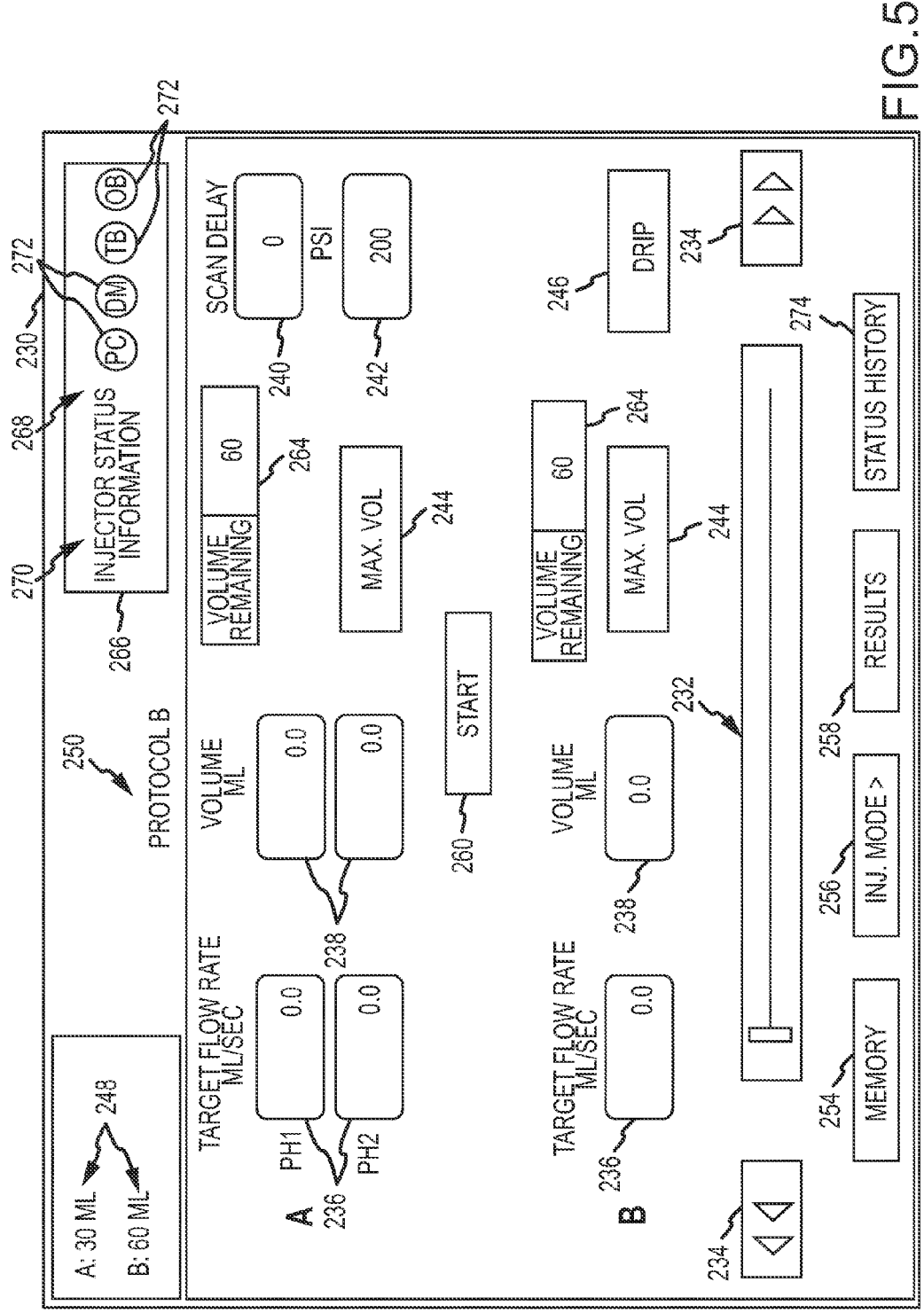
FIG. 5 is one embodiment of a setup screen for a power injector graphical user interface, and that incorporates a status message zone.
Figure 6A:
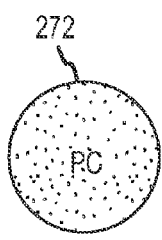
FIG. 6 displays four different representative states for an injector status icon.
Figure 6B:
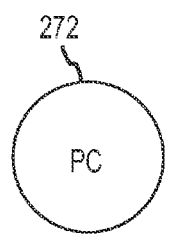
Figure 6C:
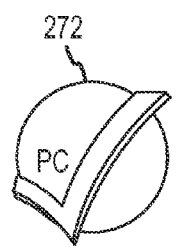
Figure 6D:
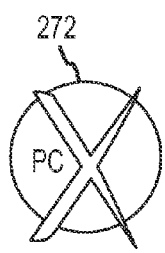

One embodiment of a setup screen is illustrated in FIG. 5 and is identified by reference numeral 230. Although the setup screen 230 may be adapted for use with any power injector configuration, it will be described herein in relation to the power injector 10 of FIG. 1 that is executing a fluid delivery protocol 126 (FIG. 3). This setup screen 230 may be presented on the graphical user interface 11 for the power injector 10 of FIG. 1. The setup screen 230 is for the case of the power injector 10 of FIG. 1 being of a dual-head configuration—utilizing a pair of syringes 28 (one defining an A side of the power injector 10, and another defining a B side of the power injector 10). Each of the A and B sides may contain any appropriate fluid (e.g., contrast media, a radio-pharmaceutical, saline, and any combination thereof). In addition, the setup screen 230 is configured for providing two phases on the A side of the power injector 10, and a single phase on the B side of the power injector 10. Any number of phases may be utilized by each of the A and B sides of the power injector 10, and the setup screen 230 may be configured accordingly. The power injector control logic 124 of FIG. 5 may be configured to store multiple setup screens 230, each of which may use a different combination of phases for the A and B sides of the power injector 10.

The setup screen 230 of FIG. 5 is configured to execute or implement the status messaging protocol 140 of FIG. 4. In this regard, the setup screen 230 includes a status message region, segment, or zone 266 in which at least one status message 268 is displayed. Each such status message 268 may be in any appropriate form. In the illustrated embodiment, the status message 268 includes a textual status message 270, along with four icons that each may be characterized as providing a graphical status message 272. In the illustrated embodiment: 1) the "PC" icon or graphical status message 272 stands for "patency check injection"; 2) the "DM" icon or graphical status message 272 stands for "drip mode injection"; 3) the "TB" icon or graphical status message 272 stands for "timing bolus injection"; and 4) the "OB" icon or graphical status message 272 stands for "OptiBolus injection." Any number of icons could be presented in the status message zone 266, and any way of making an association between an icon and one or more tasks/aspects of the fluid delivery protocol 126 may be utilized (e.g., an abbreviation as shown; via the shape of the icon). How an icon may be utilized to present status information will be discussed in more detail below in relation to FIG. 6.

The setup screen 230 also includes a status history button 274. Selecting the status history button 274 displays at least a certain number of the most recent status messages 268 that previously appeared in the status message zone 266, and in one embodiment all status messages 268 that appeared in the status message zone 266 for the fluid delivery protocol 126 that is currently being executed, for the most recent fluid delivery protocol 126, or both. This type of feature will be addressed in more detail below in relation to FIG. 8.

In one embodiment, at least one status message 268 is continually displayed or is displayed at all time in the status message zone 266 of the setup screen 230 depicted in FIG. 5. This of course does not require that the same status message 268 be continually displayed—only that status information constantly appears in the status message zone 266. In one embodiment, various different status messages 268 are displayed in the status message zone 266 of the setup screen 230 over time as the status of the power injector 10 changes for purposes of executing a fluid delivery protocol 126 (e.g., a plurality of different status messages 268 are displayed at a common location on the setup screen 230, with each such status message 268 appearing at a different point in time). In one embodiment, at least one status message 268 is continually displayed or is displayed at all times in the status message zone 266 of the setup screen 230 depicted in FIG. 5, and various different messages 268 are displayed in the status message zone 266 of the setup screen 230 over time as the status of the power injector 10 changes for purposes of executing a fluid delivery protocol 126 (e.g., a plurality of different status messages 268 are displayed at a common location on the setup screen 230, with each such status message 268 appearing at a different point in time).

The setup screen 230 from FIG. 5 may include various buttons to access various other system screens on the power injector graphical user interface 11, including a memory button 254 (e.g., for accessing an injection or fluid delivery protocol 126 that is stored), an injection mode button 256 (e.g., for selecting from a plurality of injection modes, where each injection mode has at least one phase for the A side and at least one phase for the B side), and a results button 258 (e.g., for displaying results on an injection procedure or fluid delivery protocol 126). The setup screen 230 also accommodates displaying, entering, and/or editing various parameters that relate to a fluid delivery protocol 126. The setup screen 230 may include the following: 1) a slide bar 232 for displaying/changing a value for a selected parameter presented on the setup screen 230; 2) adjustment arrows 234 for providing a more refined adjustment of a value for a selected parameter presented on the setup screen 230; 3) a pair of programmed/target flow rate segments 236 to accommodate displaying, entering, and/or editing the desired rate of delivery of contrast media or other fluid from the A side of the power injector 10 (one for each of two phases), and another programmed/target flow rate segment 236 to accommodate displaying, entering, and/or editing the desired rate of delivery of saline or other fluid from the B side of the power injector 10; 4) an injection volume segment 238 to accommodate displaying, entering, and/or editing the desired volume to be injected from the syringe 28 for each of the A and B sides of the power injector 10; 5) a remaining volume indicator 264 to depict the projected volume remaining in the syringe 28 for each of the A and B sides of the power injector 10; 6) a scan delay indicator 240 to depict the time counted down from the start of an injection or fluid delivery so that an operator may accurately delay a scanner being used in combination with the power injector 10; 7) a pressure limit segment 242 for the syringe 28 on the A side of the power injector 10; 8) a maximum volume indicator 244 for each of the A and B sides of the power injector 10, which indicates the volume currently available in the associated syringe 28, and which may blink if the volume needed for an injection or fluid delivery procedure exceeds the available volume in the associated syringe 28; 9) a drip mode button or key 246 to access a drip mode functionality for the power injector 10 (e.g., a "drip injection" being a low flow rate injection of a small volume of fluid (e.g. saline) delivered to a patient in order to keep the fluid pathway to the patient in an open condition); 10) a pair of syringe size indicators 248 for each of the A and B sides of the power injector 10; and 11) a protocol identifier 250 (e.g., to identify the injection or fluid delivery protocol being used to operate the power injector 10). Any data entry device may be utilized to enter the desired/required information and/or make a desired selection on the setup screen 230 of FIG. 5, such as a keyboard, mouse, and/or by presenting the setup screen 230 on a touch screen display. Finally, the setup screen 230 includes a start button 260 (e.g., for initiating an injection procedure or fluid delivery protocol 126).

Four icons or graphical status messages 272 appear in the status message zone 266 in the illustrated embodiment for the setup screen 230 of FIG. 5. Representative ways in which an icon or graphical status message 272 may be utilized to convey injector status information is illustrated in FIG. 6. Generally, each icon or graphical status message 272 may be presented in any one of a plurality of different states to convey status information (e.g., at least two or more different states for each icon/graphical status message 272). The icon or graphical status message 272 in part (a) of FIG. 6 is "grayed out," and which may be indicative of an inactive state for the task(s) associated with the icon (e.g., the associated task(s) is not currently being executed). The icon or graphical status message 272 in part (b) of FIG. 6 is "on," and which may be indicative of an active state for the task(s) associated with the icon (e.g., the associated task(s) is currently being executed). The icon or graphical status message 272 in part (c) of FIG. 6 includes a "check mark," and which may be indicative that the task(s) associated with the icon has been completed. Finally, the icon or graphical status message 272 in part (d) of FIG. 6 is "crossed-out," and which may be indicative of that the associated task(s) was prematurely terminated, that an error during the execution of the associated task(s), or both. Although each icon or graphical status message 272 could utilize the same number of states, such may not be required in all instances (e.g., an icon or graphical status message 272 for a patency check may utilize one number of states, while an icon or status message for a drip mode injection may utilize a different number of states).

Figure 7:
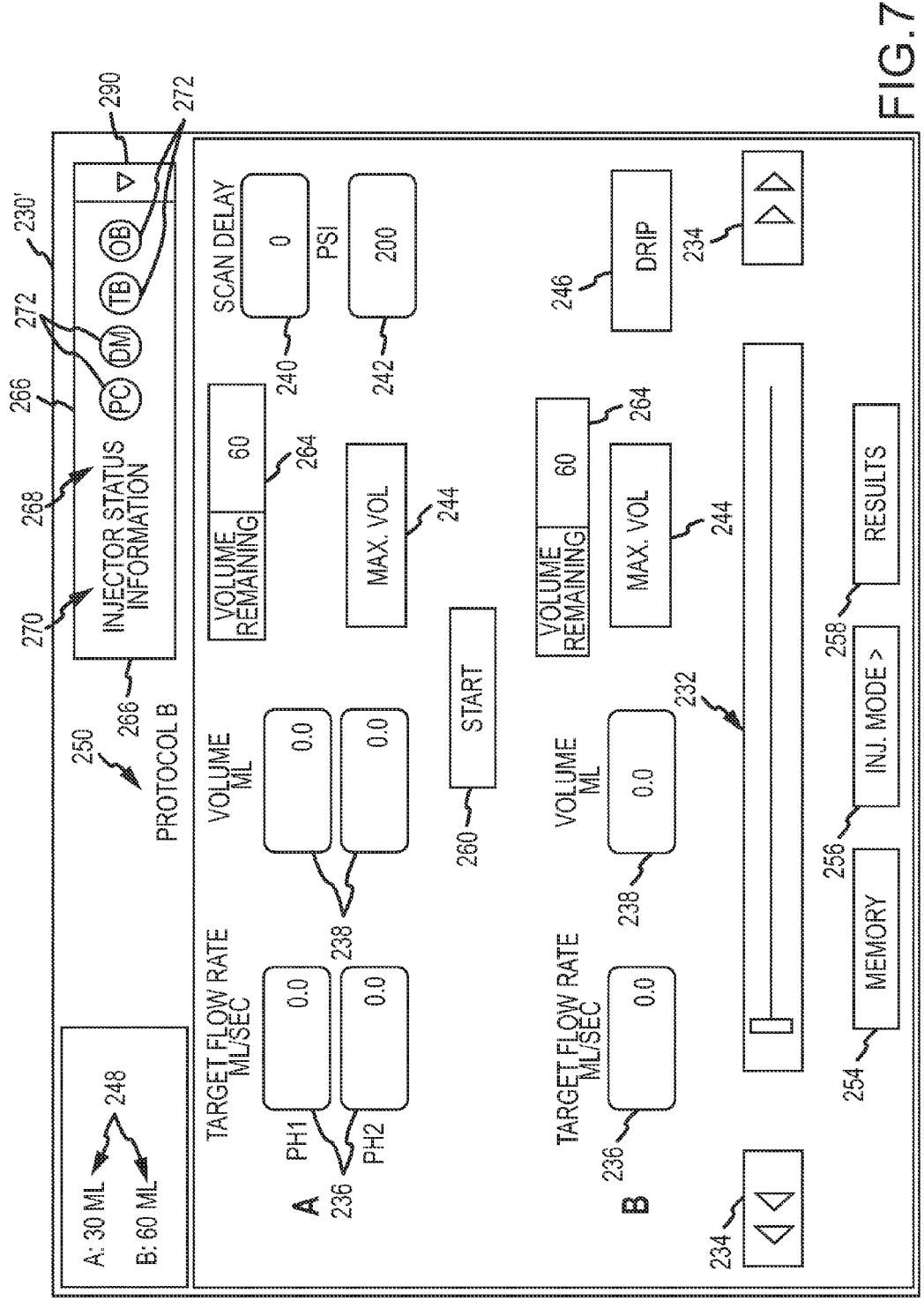
FIG. 7 is a variation of the setup screen of FIG. 5, and which includes a drop-down menu button to generate a listing of previously displayed status messages.

FIG. 7 presents a variation of the setup screen 230 of FIG. 5, and thereby utilizes a "single prime" designation. The setup screen 230' of FIG. 7 utilizes a different way for presenting a listing of status messages, compared to the setup screen 230 of FIG. 5. In this regard, the setup screen 230' of FIG. 7 includes a drop-down menu button 290. Selecting or activating the drop-down menu button 290 causes a drop-down menu window 300 to appear, and which is illustrated in FIG. 8.

Figure 8:
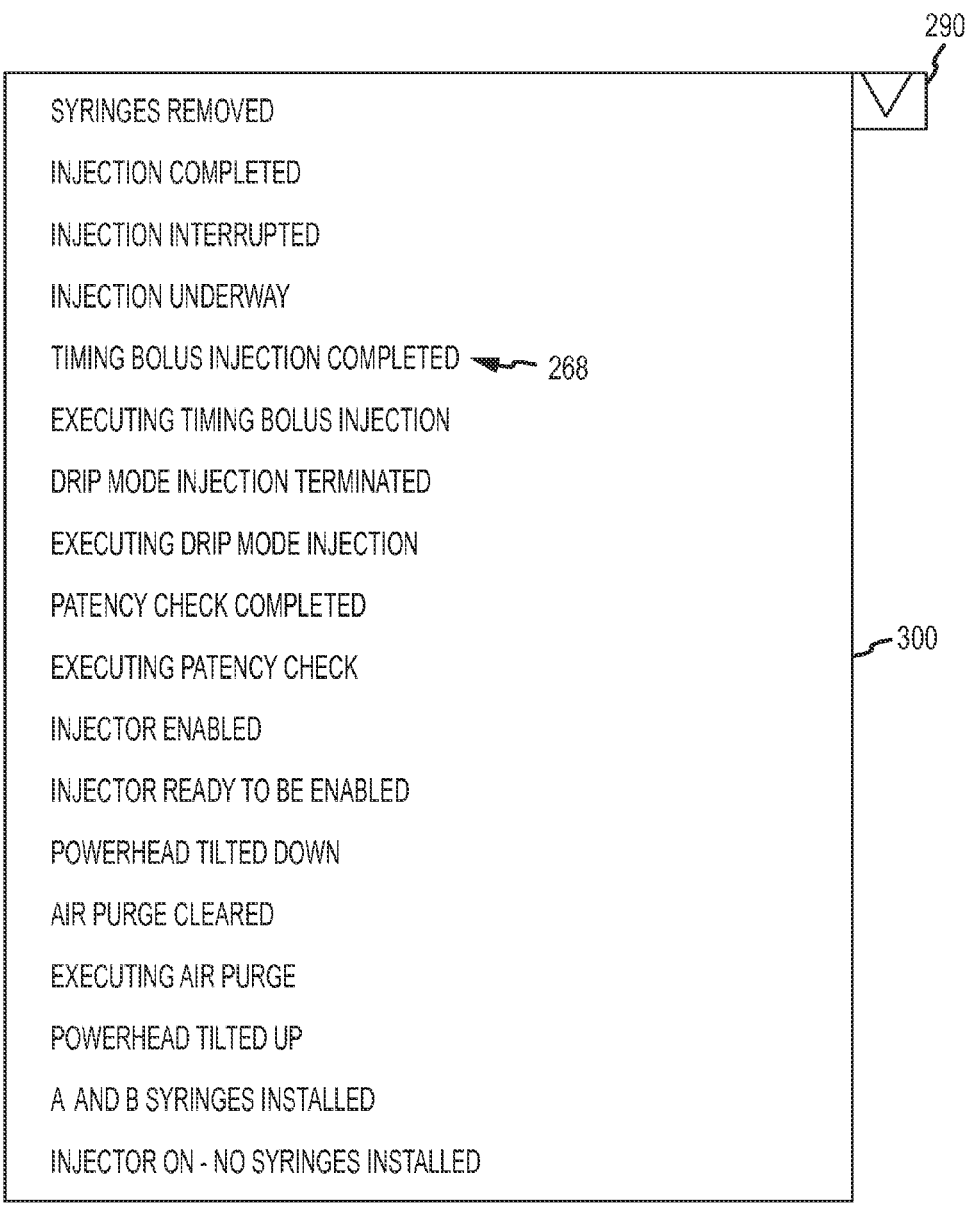
FIG. 8 is a representative listing of status messages that may be displayed when activating the drop-down menu button in FIG. 7.

The drop-down menu window 300 of FIG. 8 includes a plurality of status messages 268—the current status message 268 as well as one or more status messages that were previously displayed. Although each of the status messages 268 that are illustrated in the drop-down menu window 300 is in the form of textual status message, each status message 268 may be of any appropriate type or form. Any appropriate number of status messages 268 may be presented in the drop-down menu window 300. In one embodiment, each status message 268 that has been generated and displayed during the execution of the current or most recent fluid delivery protocol 126 (e.g., the fluid delivery procedure currently being executed) may be presented in the drop-down menu window 300. A scroll bar or the like may be utilized as desired/required to review the entire listing. Although, the status messages 268 may be listed in any appropriate order in the drop-down menu window 300 (e.g., chronological order), in one embodiment the status messages 268 are presented in reverse chronological order.

It should be appreciated that the status messages 268 shown in FIG. 8 are representative. Not all of the status messages 268 shown in FIG. 8 need be utilized, one or more other status messages 268 could be utilized, or both. For instance, one or more additional status messages 268 could be utilized: to indicate that the power injector has failed; that an injection has failed; that a "return the syringe plunger driver(s) to a "home" position operation" is being executed; and that the power injector is ready for installation of one or more syringes.

Figure 9:
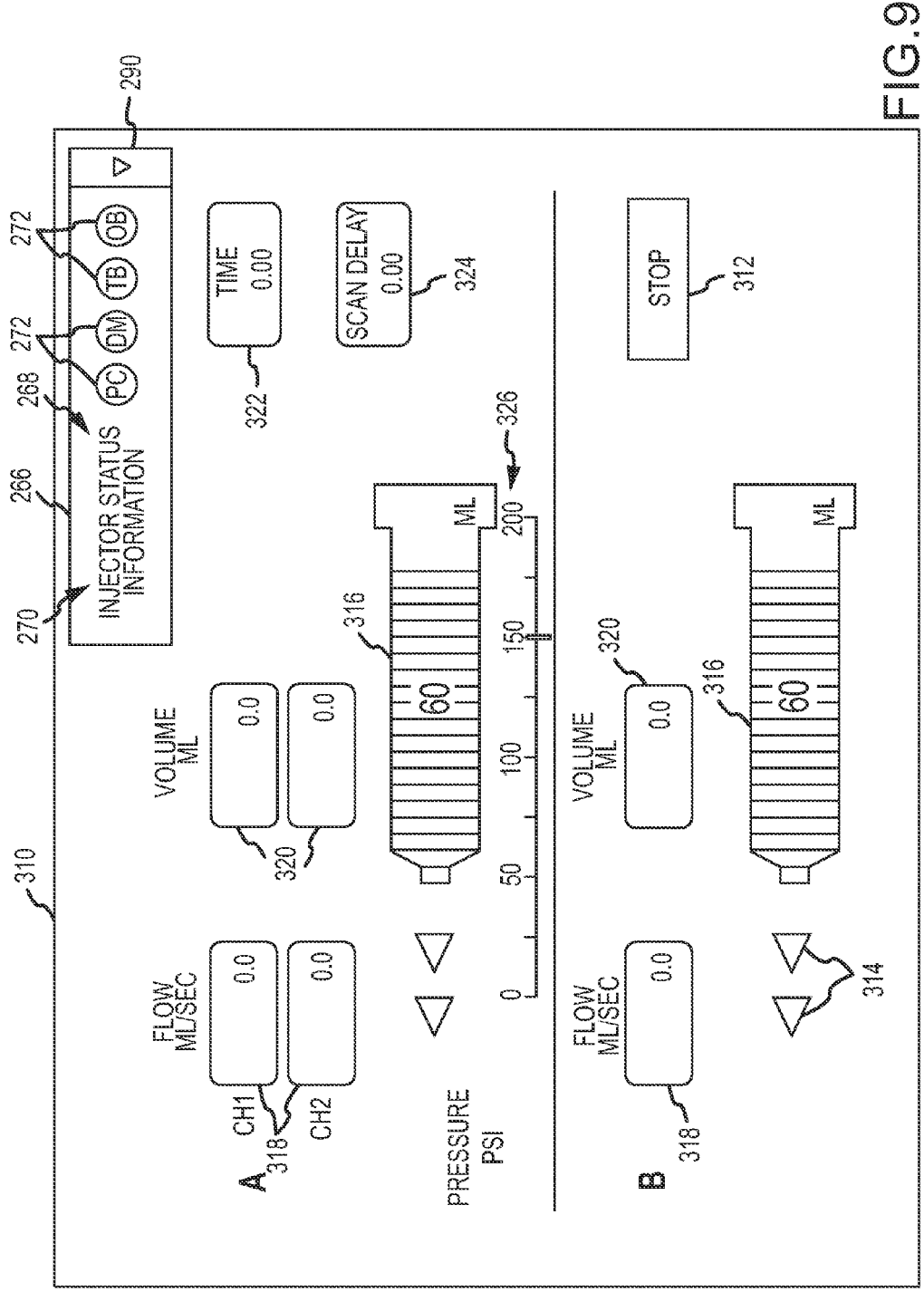
FIG. 9 is one embodiment of a progress screen for a power injector graphical user interface, and that incorporates a status message zone.

Injector status information may be presented as described above in relation to the setup screens 230, 230' of FIGS. 5 and 7, respectively. Injector status information may be displayed on any appropriate number of screens that are presented on a power injector graphical user interface. FIG. 9 is another representative screen that may be presented on a power injector graphical user interface during execution of a fluid delivery procedure (e.g., a fluid delivery protocol 126), and is in the form of a progress screen 310. The progress screen 310 includes the above-described status message zone 266, and the entirety of the above-noted discussion remains equally applicable. In one embodiment, the status message zone 266 appears at the same location on the progress screen 310 as in the case of the setup screens 230, 230'. In one embodiment, the status message zone 266 appears on each screen that is presented on a power injector graphical user interface in relation to the execution of a fluid delivery procedure (e.g., a fluid delivery protocol 126), and the status message zone 266 appears at a common location on each of these screens.

The progress screen 310 of FIG. 9 is for the case of the power injector 10 of FIG. 1 being of a dual-head configuration—utilizing a pair of syringes 28 (one defining an A side of the power injector 10, and another defining a B side of the power injector 10). In addition, the progress screen is configured for providing two phases on the A side of the power injector 10, and a single phase on the B side of the power injector 10. Any number of phases may be utilized by each of the A and B sides of the power injector 10, and the progress screen 310 may be configured accordingly.

The progress screen 310 of FIG. 9 generally displays the progress of an injection procedure or the execution of a fluid delivery protocol 126 that is currently being performed by the power injector 10. Various buttons or keys that may be selected/activated in any appropriate manner may be included on the progress screen 310 to provide any appropriate function or combination of functions, including a stop button 312 (e.g., to stop operation of the power injector 10, or more specifically the delivery of fluid from the power injector 10). The progress screen 310 also includes the following: 1) injection indicators 314 for each of the A and B sides of the power injector 10, and which may flash to indicate when fluid is being delivered from the corresponding side; 2) a remaining volume indicator 316 for each of the A and B sides of the power injector 10, and which indicates the amount of volume remaining in the associated syringe 28; 3) a programmed/target flow rate indicator 318 for each of the two phases being utilized by the fluid delivery protocol 126 on the A side of the power injector 10, and a programmed/target flow rate indicator 318 for the B side of the power injector 10, where each programmed/target flow rate indicator 318 displays the corresponding programmed/target flow rate for the fluid delivery protocol 126 currently being executed by the power injector 10; 4) a programmed volume indicator 320 for each of the two phases being utilized by the fluid delivery protocol 126 on the A side of the power injector 10, and a programmed volume indicator 320 for the B side of the power injector 10, where each programmed volume indicator 320 displays the corresponding programmed volume for the fluid delivery protocol 126 currently being executed by the power injector 10; 5) an elapsed time indicator 322 that depicts the amount of time that has passed from the start of the fluid delivery protocol 126; 6) a scan delay indicator 324 to depict the time counted down from the start of an injection so that an operator may accurately delay a scanner being used in combination with the power injector 10; and 7) a pressure indicator 326 that may show the current pressure and the pre-set pressure limit value (the vertical line representing the pre-set pressure limit value, and the horizontal line representing the current pressure).

Figure 10:
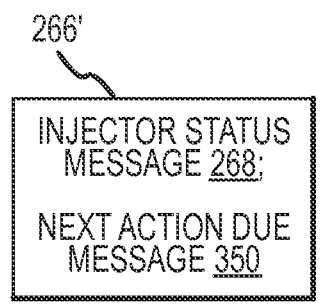
FIG. 10 is a variation of a status message zone that also displays a next action due message.

A variation of a status message zone 266 is illustrated in FIG. 10, is identified by reference numeral 266', and may be used in place of each of the message status zones 266 discussed above. In addition to including at least one injector status message 268, the status message zone 266' presents a next action due message 350. Therefore, an operator or user will not only receive information on the current status of a power injector (via the status message 268), but will also be apprised of the next action that the operator may be required to undertake in relation to the execution of a fluid delivery protocol 126. The status message history functionality discussed above in relation to the status history button 274 (FIG. 5) and the drop-down menu window 300 (FIGS. 7-8) may be utilized in relation to the status message zone 266' as well.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector, comprising:
   a powerhead;
   a syringe plunger driver;
   a first graphical user interface; and
   a setup screen presented on said first graphical user interface in conjunction with a fluid delivery protocol executable by said power injector, wherein said fluid delivery protocol comprises a programmed sequence that when executed by said power injector delivers at least one fluid to a patient, wherein said setup screen is configured to allow at least one parameter for said fluid delivery protocol to be input to said power injector, wherein said setup screen comprises a status message zone, wherein at least one status message is displayed at all times in said status message zone on said setup screen, wherein said at least one status message comprises a plurality of icons that are simultaneously presented in said status message zone on said setup screen, wherein each said icon conveys an association with a different task that pertains to execution of said fluid delivery protocol by said power injector, wherein each said icon is presentable in at least two different states within said status message zone on said setup screen, wherein presenting each said icon in each of its different corresponding states conveys a different said status message, wherein said plurality of icons comprises first and second icons such that said first and second icons are simultaneously presented in said status message zone of said setup screen, wherein each of said first and second icons is representative of an injection that is executable in conjunction with the execution of said fluid delivery protocol by said power injector, wherein said injection associated with said first icon is different from each of said fluid delivery protocol and said injection associated with said second icon, wherein said injection associated with said second icon is different from each of said fluid delivery protocol and said injection associated with said first icon, wherein said injection associated with said first icon is one of a patency check injection, a drip mode injection, an exponentially decaying flow rate injection, and an injection for determining a scan delay amount, and wherein said injection associated with said second icon is a different one of said patency check injection, said drip mode injection, said exponentially decaying flow rate injection, and said injection for determining a scan delay amount;

wherein each screen that is presented on said first graphical user interface while said power injector is in a powered on state comprises its own said status message zone, wherein said status message zone appears at a common location on each said screen that is presented on said first graphical user interface while said power injector is in said powered on state, wherein at least one said status message is displayed at all times in said status message zone on each said screen that is presented on said first graphical user interface while said power injector is in said powered on state, and wherein each said status message is reflective of a then current status of said power injector in relation to the execution of said fluid delivery protocol by said power injector; and wherein each said status message that is displayed in a corresponding said status message zone is a message that is indicative of a status that is selected from the group consisting of: that said power injector is powered on and that no syringes are installed on said powerhead, that at least one syringe is installed on said powerhead, that said powerhead is in a tilted up position, that an air purge operation is being executed, that an air purge operation has been completed, that said powerhead is in a tilted down position, that said power injector is ready to be enabled, that said power injector is enabled, that a patency check injection is being executed, that a patency check has been completed, that a drip mode injection is being executed, that a drip mode injection has been terminated, that a timing bolus injection is being executed, that a timing bolus injection has been completed, that an injection is being executed, that an injection has been interrupted, that an injection has failed, that an injection has been completed, that each syringe has been removed from said powerhead, that a "return each syringe plunger driver to a home position" operation is being executed, and that said power injector is ready to accept a number of syringes for which said power injector is configured.

2. The power injector of claim 1, wherein each said icon is presentable in each of a first state, a second state, a third state, and a fourth state within said status message zone on said setup screen, wherein presenting a given said icon in said first state conveys that its associated said task is not currently being executed, wherein presenting a given said icon in said second state conveys that its associated said task is currently being executed, wherein presenting a given said icon in said third state conveys that its associated said task has been completed, and wherein presenting a given said icon in said fourth state conveys that its associated said task was undertaken but was not completed.

3. The power injector of claim 1, wherein said at least two different states comprises first and second states, wherein said first state is an inactive state and said second state is a completed state.

4. The power injector of claim 1, wherein each said icon is presentable in at least three different states.

5. The power injector of claim 1, wherein each said icon is presentable in four different states.

6. The power injector of claim 5, wherein each said state is selected from the group consisting of an inactive state, an active state, a completed state, and a prematurely terminated state.

7. The power injector of claim 1, further comprising a listing of a plurality of status messages that have each been previously displayed in a corresponding said status message zone in relation to the execution of said fluid delivery protocol by said power injector.

8. The power injector of claim 1, wherein said at least one status message and a next action due message are simultaneously displayed in said status message zone of each said screen that is presented on said first graphical user interface while said power injector is in said powered on state.

9. The power injector of claim 1, wherein said at least one status message, that is displayed in said status message zone of each said screen that is presented on said first graphical user interface while said power injector is in said powered on state, further comprises a textual status message.

* * * * *